United States Patent [19]
Coles et al.

[11] Patent Number: 5,785,966
[45] Date of Patent: Jul. 28, 1998

[54] INHIBITION OF HUMAN XENOGENIC OR ALLOGENIC ANTIBODIES TO REDUCE XENOGRAFT OR ALLOGRAFT REJECTION IN HUMAN RECIPIENTS

[76] Inventors: John G. Coles, 162 Alexandria Boulevard, Toronto, Ontario, Canada, M4R 1M4; Miyoko Takahashi, 65 Franklin Avenue, North York, Ontario, Canada, M2N 1B8; David S. F. Young, 51 Baldwin Street, #3, Toronto, Ontario, Canada, M5T 1L1; Inka Brockhausen, 88 Fallingbrook Road, Scarborough, Ontario, Canada, M1N 2T4

[21] Appl. No.: 261,905

[22] Filed: Jun. 15, 1994

[51] Int. Cl.$^6$ ............... A61K 39/395; C07K 16/42; C12N 5/12

[52] U.S. Cl. ............... 424/131.1; 424/140.1; 424/141.1; 530/387.2; 435/327

[58] Field of Search ............... 424/131.1, 140.1, 424/141.1, 142.1; 530/387.2, 388.1; 435/327

[56] References Cited

U.S. PATENT DOCUMENTS

| | | |
|---|---|---|
| 4,137,401 | 1/1979 | Lemieux et al. |
| 4,238,473 | 12/1980 | Lemieux et al. |
| 4,541,953 | 9/1985 | Thimel-Baumer |
| 5,061,493 | 10/1991 | Ayache et al. |
| 5,560,911 | 10/1996 | Koren et al. ............... 424/131.1 |

FOREIGN PATENT DOCUMENTS

| | | | |
|---|---|---|---|
| 1042794 | 11/1978 | Canada ............... | A61K 35/12 |
| 0 498 767 | 8/1992 | European Pat. Off. | |
| 1 544 908 | 4/1979 | United Kingdom ........... | C07D 309/10 |
| PCT WO92/ 21978 | 12/1992 | WIPO | |
| PCT WO 93/03735 | 3/1993 | WIPO ............... | A61K 31/70 |
| WO 93/03735 | 3/1993 | WIPO | |
| PCT WO 93/09434 | 5/1993 | WIPO ............... | G01N 33/539 |
| PCT WO 93/16729 | 9/1993 | WIPO ............... | A61K 39/395 |
| WO 94/21799 | 9/1994 | WIPO | |
| WO 95/10303 | 4/1995 | WIPO | |

OTHER PUBLICATIONS

Downey, W. E. III et al, Transplantation, 49:160–166, Jan. 1990.
Jeffrey, L. (1992). La Presse Medicale 21:1932–1938.
Geller, R. et al. (1993). Transplantation 55:168–172.
Salame, E. et al. (1992). La Presse Medicale 21:1945–1946.
Chauhan, B. et al. (1993). Transplantation 56:443–448.
Perosa, F. et al. (1989). J. Clin. Investigat. 84:907–914.
Singal, D. et al. (1993). Immunogenetics 38:242.
Young, D. et al. (1994). Circulation 90:I419.
Vaughan, H. et al. (1995). Transplantation 59:102–109.
Polyreactivity and Antigen Specificity of Human Xenoreactive Monoclonal and Serum Natural Antibodies, Martin A. Turman et al., Transplantation, vol. 52, 710–717, 1991.
Evidence that Polyreactive Antibodies are Deposited in Rejected Discordant Xenografts, Robin L. Geller et al., Transplantation, vol. 55, 168–172, 1993.

*Primary Examiner*—Susan A. Loring
*Attorney, Agent, or Firm*—Rothwell, Figg, Ernst & Kurz, P.C.

[57] ABSTRACT

Reactivity between an alloantigen and an anti-alloantigen is indicative of immunological reactivity between two biological samples of the same species. Reactivity between a xenoantigen and an anti-xenoantigen is indicative of immunological reactivity between two biological samples of different species. In many cases both of the reactions are indicative of an antibody-mediated rejection. Anti-antibodies can be employed to reduce cross-reactivity in many transplantation-type situations, either within a similar species, or across species lines. These anti-antibodies are prepared against the antibodies responsible for the antibody-mediated rejection. These anti-antibodies can then be used in vivo or in vitro to complex with the antibodies thus reducing or eliminating reactivity between an alloantigen and an anti-alloantigen or reactivity between a xenoantigen and an anti-xenoantigen between any two species combinations. These antibodies may also be used to target and eliminate the B-cells that produce anti-xenogenic antibodies.

8 Claims, 1 Drawing Sheet

INHIBITION OF HUMAN XENOGENIC OR ALLOGENIC ANTIBODIES TO REDUCE XENOGRAFT OR ALLOGRAFT REJECTION IN HUMAN RECIPIENTS

FIELD OF THE INVENTION

This invention is directed towards anti-idiotypic antibodies which can be used for reducing allograft or xenograft rejections. This invention is also directed to methods for preparing these anti-idiotypic antibodies and methods of using these antibodies to reduce or eliminate reactivity between a xenoantigen and an anti-xenoantigen between any two species combinations, or to eliminate the B-cells that produce anti-xenogenic antibodies, or to reduce or eliminate reactivity between allogenic antigen and an anti-alloantigen. These antibodies can also be used to measure or label its cognate antibody and/or the cells that produce them and may be applied diagnostically.

BACKGROUND AND PRIOR ART

In many transplantation situations, within species, there is concern for differences between the allotype, especially the HLA type, of a cell donor and a cell recipient. In situations where allogenic cells or tissues are taken from a donor and introduced into a recipient, it is desirable that the donor and recipient be as closely HLA matched as possible. The presence in the patient's serum of antibodies against HLA antigens of the donor (donor specific cross-match), or against a high percentage of HLA alleles (PRA testing) predicts a high risk of graft rejection.

An alloantigen is a direct or indirect product of an allele which may be detected as an antigen by another member of the same species. The products of such alleles include encoded polypeptides, but also specific polysaccharides and lipids synthesized by allele encoded enzymes. Alloantigens of particular interest in the present invention include histocompatibility antigens, blood group antigens such as the ABO, Lewis group, the endothelial alloantigen system, and the like. Of special interest are histocompatibility antigens which include major, known as HLA in humans, and minor histocompatibility antigen groups. Anti-alloantigen are molecules which are capable of reacting with, or preferentially associating with, an alloantigen. Examples of such anti-alloantigens include anti-allotypic immunoglobulins or fragments thereof, anti-allotypic T-cell receptor or derivatives or fragments thereof, HLA binding peptides, etc., and combinations thereof.

Shortage of human organs is a major limitation to application of transplantation for end-stage organ disease. This has stimulated a strong interest in xenogenic transplantation. The pig has been considered by many investigators to be a suitable organ donor for human transplantation. Porcine to human xenotransplantation, however, is complicated by hyperacute rejection initiated by non-elicited human antibodies, referred to as preformed antibodies, binding to porcine xenoantigens, for example, porcine aortic endothelial cells (PAEC) xenoantigens. Other species that have been targeted for possible xenogenic transplantation into humans include sheep, goats and non-human primates.

In both examples discussed above, the problem of antibody-mediated rejection can be eliminated or reduced in severity by the use of the anti-antibodies of the present invention.

The prior art describes some success in facilitating non-xenotransplants between ABO-mismatched individuals. In human to human transplantation, the extracorporeal removal of naturally occurring anti-A and/or anti-B antibodies using a method similar to those described in several references (U.S. Pat. Nos. 4,137,401, 4,238,473; U.K. Patent 1544908; and European Patent Application 89311540.2) has enabled successful transplantation of kidneys and bone marrow between ABO mismatched individuals (Bannett, A. D., McAlack, R. P., Raja, R., Baquero, A., Morris, M.: Transplant. Proc. XIX: 4543–4546, 1987 and Bensinger, W. I., Buckner, C. D., Thomas, E. D., Clift, R. A.: Transplantation 33: 427–429, 1982).

PCT Application WO 93/03735 describes the use of at least one carbohydrate xenoantigen which is capable of binding one or more antibodies involved in a antibody-mediated xenograft rejection. The carbohydrate xenoantigen of the prior art can be used to inhibit xenoantibodies in vitro or in vivo.

In a further example, PCT Application WO 93/16729, provides an anti-human IgM antibody to lower the levels of natural antibodies which react with a xenograft in a patient who has, or is about to receive, a xenograft. In particular, this prior art discloses the production of anti-human IgM antibodies which react with the μ chain portion of the constant region of human antibodies, with such μ chain being characteristic of an IgM antibody.

The proposals of the prior art are limiting in their application as they are either directed towards removal of antibodies against identified carbohydrate antigens, or to the complete and non-specific removal of all IgM antibodies. In contrast, the present invention has adopted an approach for the removal or attenuation of anti-alloantigen antibodies or anti-xenoantigen antibodies, which is more inclusive since it can be effective against all classes of antibodies, regardless of isotype. Furthermore, the present approach is more specific since it involves depletion of only the offending alloreactive or xenoreactive antibodies, while preserving the vast majority of the total antibody complement, and thus permitting maintenance of normal immunological surveillance against infection and oncogenesis.

Geller et al. (Transplantation, Vol. 55, pp. 168–172, 1983) developed a series of hybridoma-derived monoclonal antibodies specific for the polyreactive human monoclonal antibody 103, which they had previously shown to bind efficiently to porcine endothelial cells. Their studies, however, showed that the idiotypic reagents used to block binding of monoclonal antibody 103 to endothelial cells did not show more than a 30% inhibition. They concluded by suggesting that the anti-idiotypic reagents recognized structures outside of the paratope (antigen-binding site of the mAb 103). In contrast to this prior art, the present application utilizes affinity-purified antibodies derived from human serum reactive with pig EC. Thus in the present invention, the production of murine anti-idiotypic antibodies would be based on the complete array of antibodies, representing a mixture of monoclonal specificities, which functionally react with pig EC. This would be expected to constitute a therapeutically more inclusive approach.

SUMMARY OF THE INVENTION

According to the present invention, there is provided anti-idiotypic antibodies recognizing a limited repertoire of idiotypic specificities, which recognize specific cognate antigens. These antigens can be alloantigens or xenoantigens, thereby leading to the xenogenic or allogenic reaction response in xenografts or allografts.

In one embodiment of the present invention there is provided a β-type anti-idiotypic antibody selected from the group consisting of a β-type anti-idiotypic antibody to a human anti-xenoantigen antibody, and mixtures thereof, and a β-type anti-idiotypic antibody to a human anti-alloantigen antibody, and mixtures thereof.

In another embodiment of the present invention there is provided a method for reducing or preventing graft rejection in a patient comprising contacting an effective amount of at least one β-type anti-idiotypic antibody selected from the group consisting of a β-type anti-idiotypic antibody to a human anti-xenoantigen antibody, or mixtures thereof, and a β-type anti-idiotypic antibody to a human anti-alloantigen antibody, or mixtures thereof, to reduce blood levels of said human anti-alloantigen or human anti-xenoantigen antibodies and the B-cells that produce said antibodies, in a patient in need of such reduction.

In a further embodiment, a method is provided for measuring or labelling a cognate antibody or the cells that produce said antibody using a β-type anti-idiotypic antibody selected from the group consisting of a β-type anti-idiotypic antibody to a human anti-xenoantigen antibody, and a β-type anti-idiotypic antibody to a human anti-alloantigen antibody, wherein said cognate antibody to be measured corresponds to said β-type anti-idiotypic antibody.

The present invention also provides a method for reducing or preventing graft rejection in a patient comprising contacting an effective amount of at least one antibody, or mixtures thereof, reactive against a xenoantigen, such that the xenoantigen is modified to reduce or prevent the binding of said xenoantigen to a human anti-xenoantigen antibody.

In another embodiment of the present invention there is provided a method for reducing or preventing graft rejection in a patient comprising contacting an effective amount of at least one peptide sequence homologous to a β-type anti-idiotypic antibody selected from the group consisting of a β-type anti-idiotypic antibody to a human anti-xenoantigen antibody, or mixtures thereof, and a β-type anti-idiotypic antibody to a human anti-alloantigen antibody, or mixtures thereof, to reduce or prevent the binding of said xenoantigen or alloantigen to a human anti-xenoantigen or human anti-alloantigen antibody.

DETAILED DESCRIPTION OF THE INVENTION

Figure 1:
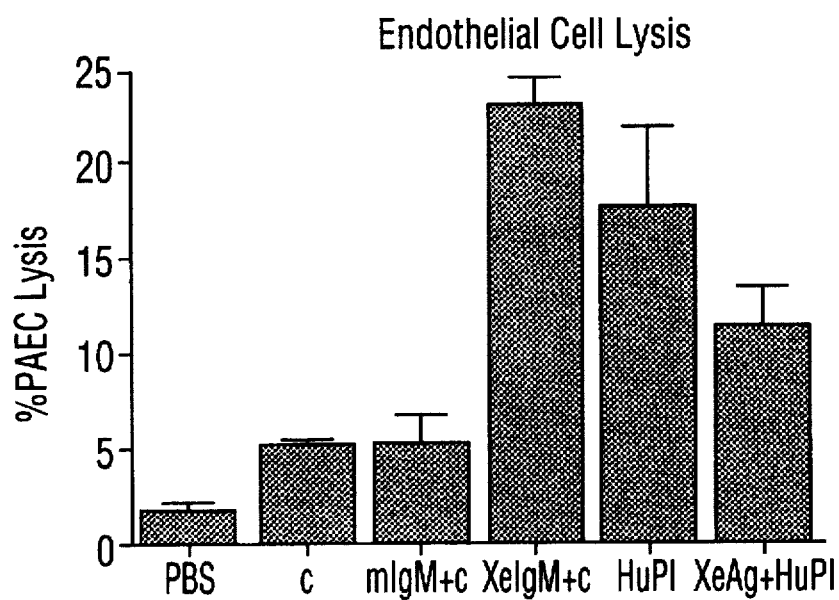
FIG. 1 shows porcine aortic endothelial cell (PAEC) lysis after incubation with either: phosphate buffered saline, human complement (C), non-xenogeneic monoclonal human IgM+C, XeIgM+C, human AB plasma, and human plasma (HuPl) preincubated with xenoantigen (XeAg).

The present invention addresses the problem of antibody-mediated rejection in the rejection of an alloantigen or xenoantigen following organ or tissue transplant within species or outside of species. The overall concept of the present invention is to prepare antibodies, either monoclonal or polyclonal, which will complex with either non-elicited or elicited human antibodies reactive against a xenoantigen or an alloantigen.

In the case of a transplant within species, the presence in the recipient's serum of antibodies against HLA antigens of the donor, will result in graft rejection. Examples of such anti-alloantigens include anti-allotypic immunoglobulins or fragments thereof, anti-allotypic T-cell receptor or derivatives or fragments thereof, HLA binding peptides and combinations thereof.

For transplantation outside of species lines, it has been found for example that porcine to human xenotransplantation is complicated by hyperacute rejection initiated by non-elicited human antibody, primarily IgM, binding to porcine aortic endothelial cell (PAEC) xenoantigens. In one embodiment of the present invention, anti-idiotypic antibodies to human xenogenic IgM may limit hyperacute rejection. This approach can also be used against all classes of xenoreactive antibodies against the xenoantigens of any species regardless of isotype including IgM, IgG, IgA, and IgE. Xenoreactive IgM against porcine xenoantigens is exemplified in the present invention, but is not to be construed as limiting. Other species that have been targeted for possible xenogenic transplantation include sheep, goats and non-human primates. The present invention can also be used to prepare β-type anti-idiotypic antibodies to a human anti-xenoantigen antibody against xenoantigens from other species.

The β-type anti-idiotypic anti-human antibody can be used according to the present invention to reduce blood levels of xenoreactive or alloreactive antibodies and the B-cells that produce them. Such reduction may be accomplished by contacting whole blood or serum of a human patient with the anti-idiotypic anti-human antibodies in either an in vivo or in vitro method. In some embodiments of the present invention, it would be useful to use a mixture of different anti-idiotypic anti-human antibodies to react with a range of different xenoreactive or alloreactive antibodies.

In one example of the present invention, in an in vivo procedure, the antibodies would be administered to a patient in an amount effective to reduce blood levels of the preformed human xenogenic antibodies, or xenoantibody producing B-cells, thus reducing or eliminating xenograft rejection.

According to this in vivo method, the anti-idiotypic anti-human antibody is administered in a pharmaceutically acceptable carrier. As representative examples of such carrier, there may be mentioned normal saline solution, buffers, etc. Such pharmaceutical carriers are well known in the art, and the selection of suitable carriers is deemed to be within of the scope of those skilled in the art from the teachings contained therein.

The anti-idiotypic anti-human antibody may be administered, for example, intravenously or intramuscularly.

In general, to inhibit or reduce xenograft rejection, the antibody according to the present invention, can be administered in an amount effective to reduce blood levels of the preformed human xenogenic antibodies, or xenoantibody producing B-cells. The treatment would preferably start at or immediately prior to the transplantation and would continue, as required.

Several recent papers have emphasized the improvement in fusion stability using immortalized human lymphocytes for the production of monoclonal antibodies using both conventional methods and clones propagated in bioreactors. The production of monoclonal Abs derived from human cell lines obviates the potential adverse HAMA response and would facilitate the regulatory process required for approval of therapeutic agents. This approach could be used to produce the human anti-human antibodies of the present invention, to eliminate any potential human anti-mouse response.

Recently described techniques of phage antibody production have allowed the manufacture in prokaryotic systems of completely human antibodies. Repertoires of antibody genes are cloned into phage, which then display functional antibody fragments on their surface and provide an efficient means for antibody selection on exposure to specific antigens. This approach could likewise be used to produce anti-idiotypic anti-human antibodies by using, for example, the xenoreactive antibody or alternatively, the xenoantigens, isolated by the methods described in this invention, as specific ligands to select recombinant antibody fragments conveyed on the surface of bacteriophage particles, according to the principles described for this bacteriophage-based screening system.

In an in vitro method, the antibodies of the present invention would be contacted with the blood or serum derived from a patient and after such treatment, the treated blood would be returned to the patient (extracorporeal circulation). Thus, for example, anti-idiotypic anti-human antibody may be supported on a suitable solid support and blood or serum derived from a patient is contacted with the supported antibody and returned to the patient.

Any one of a wide variety of solid supports may be employed for supporting the antibody in such in vitro treatment. Thus, for example, the support may be in the form of beads in a column, or a solid sheet or the like. Such techniques are generally known in the art and should be apparent to those skilled in the art from the teaching herein.

The method of the present invention for reducing blood levels of anti-xenogen antibodies or anti-allogen antibodies can be used in conjunction with other techniques to reduce or eliminate graft rejection as are known in the art.

The β-type anti-idiotypic antibodies of the present invention can also be used to measure or label its conjugate antibody and/or the cells that produce them, in a diagnostic method. For example, the anti-idiotypic antibodies of the present invention can be used as a reagent to measure the titre of the xenogenic antibody in patients preceding or following transplantation, including a xenogenic organ or tissue. Furthermore, the β-type anti-idiotypic antibodies of the present invention could be used to measure the amount of xenoreactive antibodies deposited in biosamples from transplanted grafts. In addition, the β-type anti-idiotypic antibodies of the present invention can be used to label T-cells or B-cells, producing the xenogenic antibodies, using FACS (Fluorescent-Activated Cell Sorting).

The antibodies generated against antigens, such as the porcine xenoantigens described in this method, can be used to reduce reactivity between xenoantigens and xenoantibodies. In this example, anti-porcine endothelial cell antigen antibodies may be used to reduce reactivity between xenoantigens and xenoantibodies. This may be accomplished by exposure of the monoclonal antibody to xenoantigens present on xenoantigen containing cells, either in its unmodified form or modified to render it non-complementing fixing. Such exposure and binding of the monoclonal antibodies would have the effect of modulating a reduction in antigenicity. Alternatively, these antibodies may compete with the native xenogenic antibodies for binding sites to minimize the effect of the native xenogenic antibodies.

β-type anti-idiotypic antibodies are the mirror image of their complementary antibody (AB1) and thus are topologically like the antigen that produced AB1. The peptide sequences of the monoclonal anti-idiotypic antibodies may be obtained using current peptide sequencing technology (e.g. automatic sequencers may be used to sequence overlapping peptide segments of the anti-idiotypic antibodies). The peptide sequences of the anti-idiotypic antibodies may also be derived from its DNA sequence. This may be done by constructing overlapping oligonucleotide primers to VDJ or VJ sequences of the rearranged heavy chain and light chains from cDNA libraries of the hybridomas that produce the anti-idiotypic antibodies and using PCR techniques to increase the amount of DNA needed for sequencing those genes. The DNA sequences may be expressed in an appropriate system to produce peptides or glycopeptides for use as competitive inhibitors of xenogenic antibody binding. Alternatively, peptide sequences may be chemically synthesized using currently available chemical techniques. Thus, the peptides could be used to inhibit the binding of the human xenogenic antibodies to the xenoantigens, thus reducing antibody mediated rejection.

Although the methods described herein will be described in particular detail with regard to the preparation of an anti-human IgM antibody reactive against antibodies which react with antigens on porcine aortic endothelial cells, the invention should not be construed as so limiting.

Two approaches were used for the preparation of antibodies reactive against human xenogenic IgMs (XeIgM). In one method, isolated xenogenic IgM from human plasma was used to immunize Balb/c mice for the production of murine anti-XeIgM. The second method involved the use of fixed porcine aortic endothelial cells as antigen. In this method, resulting mouse antibodies will react with the same epitope as the human xenogenic IgM. These murine antibodies are then used to inject a syngeneic mouse. The second mouse will not recognize the common component of the antibody as foreign, but will only recognize the antigen-binding site as an antigen. The antibodies from the second mouse will more effectively produce anti-idiotypic anti-human XeIgM. These two examples will be discussed in further detail below.

In the first protocol, human immunoglobulins were used to raise murine monoclonal antibodies which will bind the human immunoglobulin. In one embodiment of the present invention, the human immunoglobulins were naturally occurring xenoreactive antibodies, present in human blood which specifically bind to the antigens present on pig aortic endothelial cells (PAEC) and mediate the lysis of these cells. All isotypes including IgM, IgG, IgA, and IgE, will be included within the class of the isolated xenoreactive antibodies. In one embodiment of the present invention, xenoreactive IgM was affinity isolated using anti-μ membrane affinity chromatography with glycine elution. Before using the xenoreactive IgMs of the present invention as an antigen for the production of mouse antibodies specific against the xenoreactive IgMs, the IgMs were tested to ensure that they were xenoreactive against PAEC antigens. In addition, the XeIgMs were used to affinity isolate the xenoantigens from cultured porcine aortic endothelial cells. The authenticity of the isolated glycoproteins as xenogenic structures were confirmed by demonstrating their ability to functionally interact with and competitively inhibit human AB plasma mediated lysis of PAEC.

As mentioned previously, the purified human xenoreactive antibodies, specifically PAEC reactive IgM, were injected into Balb/c mice. Immune splenocytes were obtained from the mice and fused with SP2/0 cells to establish hybridoma lines which produce β-type anti-idiotypic monoclonal antibodies. Basic techniques for the preparation and purification of antibodies are disclosed in "Basic Principles of Antigen-Antibody Reactions", Elvin A.

Kabat, Methods in Enzymology, Vol. 70, (1980), pp. 3–70, including the procedure for the production of monoclonal antibodies which are described by G. Kohler and C. Milstein, in Nature (London), Vol. 256, (1975), p. 495, and Eur. J. Immunol. (1976), 6:511–519; all of which are incorporated herein by reference. Briefly, fused cell in selective medium containing hypoxanthine, aminopterin, and thymidine were added to 300–5000 wells of tissue culture plates, which were preseeded with feeder cells. Hybridoma cultures were subcloned 2–3 times by limiting dilution method on a feeder layer of $1-3 \times 10^4$ mouse peritoneal macrophages. Monoclonal or polyclonal antibodies can be prepared according to the present invention, although monoclonals are exemplified. Anti-idiotypic antibodies can be prepared from the serum of animals such as rabbits, horses, or goats, which have been immunized against the appropriate antigens (i.e. immunoglobulins).

Immunoglobulins contain antigen-combining sites that determine the binding specificity of the antibody and are themselves immunogenic. These serologically defined epitopes are described as idiotypes. The collection of idiotopes on an immunoglobulin make up its idiotype and antibodies elicited against them are referred to as anti-idiotypic antibodies. The humoral response to a syngeneic immunoglobulin contains anti-idiotypic antibodies that fall into two classes, those recognizing idiotopes that lie within the antigen binding site of the first immunoglobulin (βanti-idiotypes) and those recognizing idiotopes that lie outside this region (αanti-idiotypes or anti-framework antibodies). The humoral response to a non-syngeneic immunoglobulin will also include antibodies against allotypic determinants which complicate the screening of hybridoma culture supernatants for the presence of anti-idiotypic antibodies. Therefore, it is necessary to remove mouse anti-human allotypic antibodies prior to screening for anti-idiotypic antibodies.

In the second procedure, fixed whole PAECs were injected into Balb/c mice for an in vivo immunization. In addition, in vitro immunizations were done by co-culturing non-immunized splenocytes with fixed PAEC. Both were fused to SP2/0 myeloma partners. The resulting monoclonal antibodies inhibit the binding of human xenogenic IgMs to PAEC, demonstrating that the monoclonal antibodies bind the same epitopes that are recognized by the human xenogenic IgM. As mentioned previously these monoclonal antibodies can be used directly to inhibit or reduce the binding of human xenogenic IgMs to the corresponding xenoantigen, thus reducing xenograft rejection.

The mouse monoclonal antibodies, produced using this second procedure, were then used as an antigen to immunize a syngeneic mice strain. The use of inbred mouse strains will therefore avoid the allotype response and will facilitate the production of anti-idiotypic antibodies. The resulting hybridoma cultures are screened for β-type anti-idiotypic activity.

The following examples are offered by way of illustration and not by limitation.

EXAMPLES

Example 1

Isolation of Functional Xenoantigens from Porcine Aortic Endothelial Cells and Validation of Xenoreactivity by Functional Assays Fresh porcine aortic segments were blocked with concentrated plasma ultrafiltrate between 10,000 and 100,000 kD MW. Human AB plasma was incubated with the aortic segments and eluted with glycine HCl pH2.3 or 3M NaSCN. Xenoreactive IgM was affinity isolated using anti-μ membrane affinity chromatography (MAC) and glycine elution. The XeIgM was immobilized on a MAC disc and used to affinity isolate xenoantigens derived from cultured porcine aortic endothelial cells (PAEC) in 10% FCS detergentized in 0.5% Triton X-100. The XeAg was resolved with SDS gel electrophoresis using 8–16% Tris-glycine gels and a discontinuous buffer system. The gels were stained with Coomasie brilliant blue or transferred to polyvinylidenedifluoride membranes for immunoblotting with human AB plasma and horse radish peroxidase conjugated rabbit anti-human μ antibodies and developed with enhanced chemiluminescence (ECL).

The functional capability of isolated IgM to mediate complement dependent xenogenic lysis of PAEC was confirmed in an endothelial cell lysis assay. PAEC lysis was determined in endothelial cells grown to confluency in 96 well microtitre plates by ethidium homodimer uptake after incubation with: phosphate buffered saline, human complement (C), non-xenogeneic monoclonal human IgM+C, XeIgM+C, human AB plasma, and HuPl preincubated with XeAg.

Xeno-IgM reconstituted with complement lysed PAEC to the same extent as human AB plasma at 1:8 dilution. This is shown in FIG. 1.

Coomasie blue stained gels of XeIgM isolated xenoantigens resolved with SDS gel electrophoresis revealed several discrete bands: a triplet between 30–55 kD, 90 kD and a doublet at 110 kD MW. The xenoantigenicity of these proteins were confirmed with Western blotting using human AB plasma. The authenticity of the isolated proteins as xenogeneic structures was confirmed by demonstrating their ability to functionally interact with and competitively inhibit AB plasma mediated lysis of PAEC (FIG. 1). This demonstrates that the IgM isolated by the method in this invention is an authentic xenoreactive antibody, which has the capacity to produce lysis of PAEC comparable to that observed with human plasma.

IgM isolated by this method retains the capability of fixing complement and mediating xenogeneic endothelial cell lysis. The specificity of these antibodies were confirmed by demonstrating selective absorption to porcine aortas. Antigens isolated using these xenoantibodies are functional, as demonstrated by their capacity to inhibit xenogeneic lysis of PAEC by human plasma, and are representative of endothelial cell surface determinants. The disparity in molecular weight of xenoantigens reported thus far may be due to strain specific porcine xenoantigens, individual variations in human xenoreactive antibodies, different culture conditions of various porcine tissue, and differential glycosylation of porcine antigens.

Example 2

Mouse Anti-Idiotypic Antibodies Prepared from Isolated XeIgM

Affinity isolated XeIgM from human plasma absorbed to fresh porcine aortas was used to immunize Balb/c mice that were boosted at 2 weeks. The mice were sacrificed at 6 weeks and the serum and spleens were harvested. Hybridomas from PEG fusion of immunized mice spleen cells with Sp2/0 myeloma partners were produced. Clone 4XM-24 (deposited with American Type Culture Collection, 12301 Parklawn Drive, Rockville, Md. 20852, USA, under Accession Number HB 11658, on Jun. 14, 1994) produced IgM, k isotype, and clone 4XM-23 (deposited with American Type Culture Collection, 12301 Parklawn Drive, Rockville, Md. 20852, USA, under Accession Number HB 11657, on Jun. 14, 1994) produced IgG 2a, k isotype, and both have been injected into mice for ascites production.

Inhibition of human IgM (huIgM) binding to cultured porcine aortic endothelial cells was tested in a cellular ELISA by incubating human plasma with: 1) mouse anti-XeIgM serum; 2) mouse anti-XeIgM serum absorbed against human anti-A and anti-B coated RBC's to remove antibodies against non-xenogeneic determinants; 3) hybridoma supernatant. Serum from mice immunized with antigens not related to IgM (e.g. Troponin-T) and Sp2/0 supernatant were used as controls.

Figure 2:
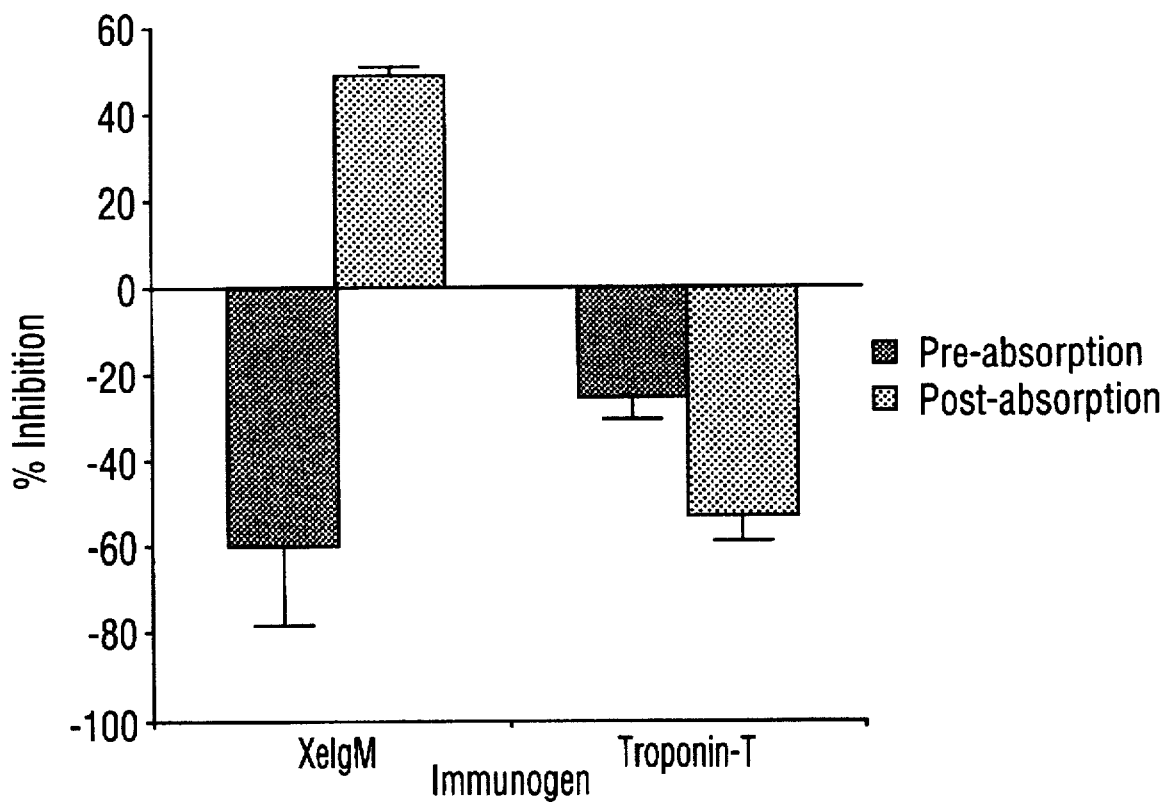
FIG. 2 shows the effect of mouse sera following immunization with human-xenoreactive IgM (XeIgM) and Troponin-T (control) on binding of human IgM to PAEC.

FIG. 2 shows the effect of sera from mice immunized with affinity-isolated human xenoreactive IgM on the binding of human IgM to porcine aortic endothelial cells measured in a cellular ELISA. Non-absorbed mouse serum showed approximately 61% enhancement of human IgM binding at 1:8 dilution. Following absorption, serum from XeIgM-immunized mice showed approximately 50% inhibition of human IgM binding to PAEC. Absorbed sera from troponin-T (control) sera did not exhibit inhibition of IgM binding.

Six clones derived from the splenocytes of this mouse inhibited human IgM binding by 28%-31% and were propagated after limiting dilution cloning. This implies that the inhibition of human IgM binding by the anti-idiotypic monoclonal antibodies was not an artifact of cloning since the sera of the mouse also produced inhibition of human IgM binding. In another example up to 85% of subclones, after three rounds of limiting dilution cloning, produced at least 30% inhibition of human IgM binding to PAEC implying stability and clonality.

The pI values of clones 4XM-23 and 4XM-24 were 7.4 and 7.1, respectively. It has been noted that 4XM-23 and 4XM-24 do not bind to PAEC directly (as determined by cellular ELISA), thus the inhibition of human XeIgM binding is due to fluid phase interactions, and not cell surface interactions. This supports the finding that the MX antibodies are anti-idiotypic antibodies that bind to human XeIgM.

Absorbed mouse anti-idiotypic anti-XeIgM Abs strongly inhibited the binding of XeIgM to PAEC, indicating that monoclonal anti-XeIgM anti-idiotypic Abs may limit rejection of porcine to human transplants.

Example 3
Mouse Anti-Idiotypic Antibodies Prepared from Gluteraldehyde fixed PAECs The strategy of using mouse anti-porcine antibodies that are cross reactive with human xenoreactive IgM to immunize syngeneic mice was used according to the protocol described below. This results in the production of anti-idiotypic anti-human xenoreactive IgM while avoiding a non-specific mouse anti-human response as well as eliminating the anti-mouse anti-framework (alpha) response.

In vivo immunizations were performed using gluteraldehyde fixed PAECs injected into Balb/c mice and boosted three weeks later. The mice were sacrificed 3-4 days after additional pre-fusion boost and the spleen harvested. Fifteen primary hybridization cultures from the in vivo immunized mice were subjected to repetitive limiting dilution cloning. Twelve cultures showed competitive inhibition of XeIgM binding (7.5%-43.1%) after the second round of cloning. These were stable after the third round of cloning since 32%-100% of the subclones produced at least 10% XeIgM inhibition.

One way of speeding up the immunizations required to produce the polyclonal response to the starting antigen and subsequently the anti-idiotypic response is to use in vitro immunization. In vitro immunizations were done by co-culturing non-immunized splenocytes with gluteraldehyde fixed PAEC. Splenocytes are PEG fused with non-Ig secreting Sp2/0 myeloma partners and subjected to limiting dilution cloning. Two in vitro immunized hybridomas were stable after three rounds of limiting dilution cloning.

A competitive cellular ELISA detecting human IgM from human AB plasma binding to PAEC in the presence of hybridoma supernatant is carried out to demonstrate cross reactivity of the monoclonal antibody to human XeIgM.
Protocol: PAEC-hybridoma Culture Screening Hybridoma culture supernatants are screened for the presence of monoclonal antibodies which compete with human-xeno-IgM for the epitope(s) on PAEC.

A competitive ELISA measures binding of human xenoreactive IgM to porcine aortic endothelial cell monolayers. The PAEC are fixed with 0.01% gluderaldehyde and cultured in 96-well plates. Whole human AB plasma diluted ⅛ in (dilution buffer consisting of phosphate buffered saline with 0.25% bovine serum albumin, pH 7.4) was used as a source of human xenoreactive IgM. The secondary labeling antibody was peroxidase-conjugated donkey anti-human IgM.

PAEC plates were washed three times with wash buffer (PBS with 0.05% Tween 20). Fifty microliters of sample supernatant and appropriate controls were added to the plate and incubated at 37° C. for 30 min. Then 50 uL of human xeno-IgM (⅛ dilution of AB plasma) was added and incubated for 60 min. at 37° C. The plates were washed 3 times with wash buffer and 100 uL of OPD was added to all wells and allowed to hydrolyse for 30 min at room temperature in the dark. The plates were read in an Elisa plate scanner after the reaction was stopped with 2M $H_2SO4$.

Dilution buffer was used as the control. Combinations of some of the hybridoma supernatants produced additive effects inhibiting up to 80% of XeIgM binding. These results are shown in Table 1. Clone 4EC-21 (deposited with the American Type Collection, 12301 Parklawn Drive, Rockville, Md. 20852, USA, under Accession Number HB 11656, on Jun. 14, 1994), produced by IgG, 1, k isotype.

TABLE 1

Summary of Results

| Samples | $\bar{X}$ $OD_{490\,nm}$ | % Inhibition of h-xeno IgM binding vs DB (PBS, 0.25% BSA) (100% binding) |
|---|---|---|
| EC 3 | 0.172 | 21 |
| EC 7 | 0.173 | 21 |
| 2EC 9 | 0.161 | 25.8 |
| 2EC 10 | 0.124 | 42.9 |
| 2EC 11 | 0.164 | 24.4 |
| 4EC 21 | | 49.0 |
| EC 3 + 7 | 0.121 | 44.2 |
| EC 3 + 7 + 2EC 9 | 0.126 | 41.9 |
| EC 3 + 7 + 2EC 9 + 10 | 0.136 | 37.3 |
| EC 3 + 7 + 2EC 9 + 10 + 11 | 0.045 | 79.3 |

Dilution Buffer: $\bar{X}$ $OD_{490\,nm}$ = 0.217 (n = 3, SD-0.023, CV-10.8%)

Although the disclosure describes and illustrates preferred embodiments of the invention, it is to be understood that the invention is not limited to these particular embodiments. Many variations and modifications will now occur to those skilled in the art. For a definition of the invention, reference is to be made to the appended claims.

We claim:

1. A method for reducing xeno-graft rejection in a patient comprising treating the blood of said patient with an effective amount of at least one β-type anti-idiotypic antibody reactive to a human anti-xenogenic antibody, or mixtures thereof, to reduce blood levels of said human anti-xenogenic antibody, and the B-cells that produce said antibodies in a patient in need of such reduction; wherein said β-type anti-idiotypic antibody is prepared by a method comprising:

preparing a mouse monoclonal antibody to a xenoantigen, wherein said xenoantigen is reactive against said human anti-xenogenic antibody;

using said monoclonal antibody as an antigen to immunize a syngeneic mouse to prepare an anti-idiotypic antibody; and isolating a β-type anti-idiotypic antibody.

2. The method according to claim 1 wherein said β-type anti-idiotypic antibody, or mixtures thereof are administered to said patient in a suitable pharmaceutical carrier.

3. The method according to claim 1 wherein said β-type anti-idiotypic antibodies are used in vitro using extracorporeal circulation.

4. The method according to claim 1 wherein said xenoantigen is porcine aortic endothelial cells.

5. The method according to claim 1 wherein said mouse monoclonal antibody to a xenoantigen is hybridoma 4EC-21 (ATCC HB 11656).

6. A method for reducing xeno-graft rejection in a patient comprising treating the blood of said patient with an effective amount of at least one β-type anti-idiotypic antibody reactive against a human anti-xenogenic antibody, or mixtures thereof to reduce the binding of said xenoantigen to said human anti-xenoantigenic antibody, wherein said β-type anti-idiotypic antibody is prepared by a method comprising:

preparing a mouse monoclonal antibody to a xenoantigen, wherein said xenoantigen is reactive against said human anti-xenogenic antibody;

using said monoclonal antibody as an antigen to immunize a syngeneic mouse to prepare an anti-idiotypic antibody; and isolating a β-type anti-idiotypic antibody.

7. The method according to claim 6 wherein said xenoantigen is porcine aortic endothelial cells.

8. The method according to claim 6 wherein said antibody is produced from hybridoma 4EC-21 (ATCC HB 11656).

* * * * *